United States Patent [19]

Nakayama et al.

[11] 4,448,603
[45] May 15, 1984

[54] HERBICIDAL COMPOSITION

[75] Inventors: Haruhiko Nakayama, Kashiwa; Takashi Tatsuno, Tokyo, both of Japan

[73] Assignee: Rikagaku Kenkyusho, Wako, Japan

[21] Appl. No.: 292,642

[22] Filed: Aug. 13, 1981

[30] Foreign Application Priority Data

Aug. 21, 1980 [JP] Japan .................................. 55-115286
Aug. 21, 1980 [JP] Japan .................................. 55-115287
Jul. 27, 1981 [JP] Japan .................................. 56-117267

[51] Int. Cl.$^3$ ............................................ A01N 43/64
[52] U.S. Cl. .......................................... 71/92; 548/266
[58] Field of Search ............................. 71/92; 548/266

[56] References Cited

PUBLICATIONS

Kubota et al., Chemical and Pharmaceutical Bulletin, vol. 19 (1971), No. 6, pp. 1226–1233.

Primary Examiner—Catherine L. Mills
Attorney, Agent, or Firm—Bucknam and Archer

[57] ABSTRACT

This invention relates to a herbicidal composition comprising 3-[3-(4H-1,2,4-triazolyl)amino]-1-(3H)-isobenzofuranone (A) as an effective ingredient and to a herbicidal composition comprising the compound (A) and at least one compound selected from the group consisting of α,α,α-trifluoro-2,6-dinitro-N,N-dipropyl-p-toluidine (B), 2-(3′,4′-dichlorophenyl)-4-methyl-1,2,4-oxadiazolidine-3,5-dione (C) and 2,4-bis(isopropylamino)-6-methylthio-s-triazine (D) as effective ingredients.

3 Claims, No Drawings

HERBICIDAL COMPOSITION

BACKGROUND OF THE INVENTION

1. Field of the Invention

This invention relates to a herbicidal composition and more particularly to a herbicidal composition comprising 3-[3-(4H-1,2,4-triazolyl)amino]-1-(3H)-isobenzofuranone (A) as an effective ingredient and to a herbicidal composition comprising the compound (A) and at least one compound selected from the group consisting of α,α,α-trifluoro-2,6-dinitro-N,N-dipropyl-p-toluidine (B), 2-(3',4'-dichlorophenyl)-4-methyl-1,2,4-oxadiazolidine-3,5-dione (C) and 2,4-bis(isopropylamino)-6-methylthio-s-triazine (D) as effective ingredients.

2. Description of the Prior Art

It is known that 3-amino-1,2,4-triazole has herbicidal activity. However, 3-amino-1,2,4-triazole shows non-selective herbicidal action due to its too large absorbability against and migration rate in a plant body and therefore it has been a problem that the compound had phytotoxicity on cultivated plants in practical use.

In the light of the problem mentioned above, the inventors have studied the matter and found that one of the derivatives of 3-amino-1,2,4-triazole, that is, 3-[3-(4H-1,2,4-triazolyl)amino]-1-(3H)-isobenzofuranone shows reduced phytotoxicity and further, the compound in combination with at least one compound selected from the group consisting of α,α,α-trifluoro-2,6-dinitro-N,N-dipropyl-p-toluidine (B), 2-(3',4'-dichlorophenyl)-4-methyl-1,2,4-oxadiazolidine-3,5-dione (C) and 2,4-bis(isopropylamino)-6-methylthio-s-triazine (D) exhibits a synergistic effect and reduces the problem of residue in soil. The inventors has accomplished this invention based on the discoveries described above.

SUMMARY OF THE INVENTION

This invention relates to a herbicidal composition comprising 3-[3-(4H-1,2,4-triazolyl)amino]-1-(3H)-isobenzofuranone (A) as an effective ingredient and to a herbicidal composition comprising the compound (A) and at least one compound selected from the group consisting of α,α,α-trifluoro-2,6-dinitro-N,N-dipropyl-p-toluidine (B), 2-(3',4'-dichlorophenyl)-4-methyl-1,2,4-oxadiazolidine-3,5-dione (C) and 2,4-bis(isopropylamino)-6-methylthio-s-triazine (D) as effective ingredients.

DESCRIPTION OF THE PREFERRED EMBODIMENTS

The invention will now be described in detail.

One of the effective ingredient of the herbicidal composition according to this invention is 3-[3-(4H-1,2,4-triazolyl)amino]-1-(3H)-isobenzofuranone (A) of the following formula:

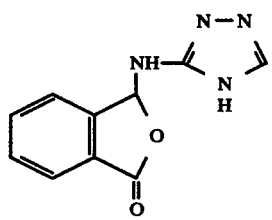

The compound (A) is a substitution product of 3-amino-1,2,4-triazole and has a water-solubility of 2.3% which is remarkably lower than that of 3-amino-1,2,4-triazole (28%) and therefore, it exhibits improved and selective absorbability against and migration rate in a plant body. Accordingly, the compound may suitably be used as an effective ingredient of a herbicide useful for various kinds of cultivated plants, particularly for cotton without any phytotoxicity. In addition, the compound has an excellent herbicidal activity to gramineous weeds such as large crabgrass and annual bluegrass and, broadleaf weeds such as slender amaranth, lawn pennywort, common purslane and prostrate superge.

The compound used in this invention, that is, 3-[3-(4H-1,2,4-triazolyl)amino]-1-(3H)-isobenzofuranone (A) may be prepared, for example, according to the following reaction:

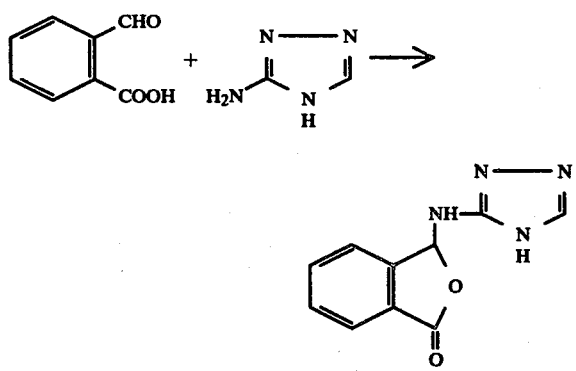

wherein equal moles of o-formyl benzoic acid and 3-amino-1,2,4-triazole are reacted at a temperature of from 50° C. to 150° C. with stirring in a suitable inert solvent such as alcohols such as methanol and ethanol, aromatic hydrocarbons such as benzene and toluene, aliphatic hydrocarbons such as hexane and heptane, and halogenated hydrocarbons such as carbon tetrachloride. On the other hand, the compound (B) is known as an effective herbicide for cotton, soybean, carrot, potato, fruits or vegetables and it alone is generally applied in an amount of from 0.5 to 1.0 kg/ha. The compound (C) alone is generally applied to cotton, garlic, onion, potato, fruits and citrus as a herbicide, in an amount of from 1.5 to 10 kg/ha. The compound (D) alone is generally applied to cotton, celery, pea and potato as a post-treatment herbicide, in an amount of from 0.3 to 1.0 kg/ha.

In general, the compounds (A), (B), (C) and (D) show a herbicidal activity on both gramineous and broadleaf weeds, when they are used in the amount set forth above. If the amount used is lower, the herbicidal effect does not appear, while if the amount is higher, an undesirable phytotoxicity is revealed.

The use of the compound (A) in combination with the compounds (B), (C) or (D) results in the expansion of the herbicidal applications, a decrease in an amount of the compounds (A), (B), (C) and (D) used, and the reduction of the residue of the compounds (B), (C) and (D) in soil.

In this invention, the compound (A) or a mixture of the compound (A) and at least one compound selected from the group consisting of the compounds (B), (C) and (D) may be used. However, the compound (A) or the mixture may generally be diluted with an inert liquid or solid carrier, if necessary, adding a surface active agent and may be used in the form of an emulsion, dust, wettable powder, granules and the like.

Liquid carriers used in this invention include various kinds of organic solvents such as hydrocarbons such as kerosene, benzene and xylene, halogenated hydrocarbons such as chlorobenzene and dichloroethylene, alcohols such as methanol and ethanol and ketones such as acetone. Examples of solid carriers used in this invention are bentonite, kaolin, clay, talc, acid clay, diatomaceous earth, silica sand and calcium carbonate. Examples of surface active agents include alkylbenzenesulfonates, ligninsulfonates, higher alcohol sulfonates, polyoxyethylene fatty acid esters, polyoxyethylene sorbitan fatty acid esters, dialkyl sulfosuccinates, and alkyl trimethyl ammonium chlorides.

An appropriate mixing ratio of the effective ingredient(s) is about 10 to about 90% in case of an emulsifiable liquid or wettable powder and about 0.1 to about 10% in case of a dust or granules. Of course, the mixing ratio of the effective ingredient(s) may be changed according to the intended use.

A herbicidal composition comprising the compound (A) as an effective ingredient according to this invention may be applied to the soil or the stem or the leaf. When applied to the soil, the herbicide may uniformly be sprinkled on the soil surface in an amount of from 1.0 to 5.0 kg of an effective ingredient per ha. When applied to the stem or the leaf, a 0.1 to 0.5 weight percent solution of an effective ingredient may uniformly be sprinkled in an amount of 500 to 2000 liter/ha, preferably in the 4 to 5-leaf-stage of the cultivated plant.

When a herbicidal composition comprising the compounds (A) and (B) as effective ingredients is applied, it may be used in an amount of from 1.0 to 5.0 kg/ha of the compound (A) and from 0.1 to 1.0 kg/ha, preferably 0.1 to 0.5 kg/ha of the compound (B), respectively.

When the compound (C) or (D) is employed in combination with the compound (A), the compounds (A) and (C) or (D) may be applied in an amount of from 0.4 to 1.5 kg/ha and from 0.1 to 0.5 kg/ha, preferably from 0.5 to 1.0 kg/ha and from 0.2 to 0.3 kg/ha, respectively.

A combination of the compound (A) with the compounds (B), (C) or (D) according to this invention gives an improved herbicidal composition which shows a high synergistic effect and reduces the problem of residue thereof in soil.

Further, the herbicidal composition comprising the compound (A) in combination with the compounds (B), (C) or (D) may also be applied, without any phytotoxicity, to the cultivated plants such as soybean and sunflower which would suffer from phytotoxicity if the compound (A) alone were applied.

The present invention will now be described in detail with reference to the following Examples to which the present invention should not be limited within the gist thereof.

The preparation of
3-[3-(4H-1,2,4-triazolyl)amino]-1-(3H)-isobenzofuranone o-Formyl benzoic acid (15 g, 0.1 mole) was dissolved in methanol (200 ml). 3-Amino-1,2,4-triazole (8.4 g, 0.1 mole) was added to the solution and the mixture was refluxed with stirring for 60 minutes. After cooling, 12.5 g of 3-[3-(4H-1,2,4-triazolyl)amino]-1-(3H)-isobenzofuranone (the compound (A)) was crystallized out and the filtrate was concentrated to further give 7.8 g of (A) as crystal. The resulting crystal of (A) (20.3 g, yield 94%), m.p. 250°–254° C. Recrystallization from methanol, m.p. 252°–254° C.

| Elemental Analysis | C | H | N |
|---|---|---|---|
| Calculated for $C_{10}H_8O_2N_4$ | 55.55 | 3.73 | 25.92 |
| Found | 55.76 | 3.60 | 25.84 |

FORMULATING EXAMPLE 1

50 Parts by weight (parts by weight) of 3[-3-(4H-1,2,4-triazolyl)amino]-1-(3H)-isobenzofuranone (the compound (A)), 45 parts by weight of diatomaceous earth and 5 p.b.w. of Solbol 8070 (a surface active agent produced by TOHO CHEMICAL INDUSTRY Co., Ltd.) were homogeneously mixed to give a wettable powder containing 50% effective ingredient.

FORMULATING EXAMPLE 2

50 Parts by weight of the compound (A)/$\alpha,\alpha,\alpha$-trifluoro-2,6-dinitro-N,N-dipropyl-p-toluidine (the compound (B)) mixture of a given ratio, 45 parts by weight of diatomaceous earth and 5 parts by weight of Solbol 8070 were homogeneously mixed to give a wettable powder containing 50% effective ingredient.

FORMULATING EXAMPLE 3

The procedure of Formulating Example 2 was repeated to give a wettable powder except 2-(3',4'-dichlorophenyl)-4-methyl-1,2,4-oxadiazolidine-3,5-dione (the compound (C)) or 2,4-bis(isopropylamino)-6-methylthio-s-triazine (the compound (D)) were used instead of the compound (B).

EXAMPLE 1

Polyethylene vats of 1/1480 ares were charged with the field soil on which cotton seeds were sowed and then, 2 cm thick soil containing weed seeds was placed thereon. Then, a given amount of a wettable powder prepared in Formulating Example 1 was uniformly sprinkled on the soil surface in the first-leaf-stage of cotton. On 20th day after seeding, a herbicidal effect and phytotoxicity to cotton were observed.

The results are given in Table I.

TABLE I

| Amount sprinkled (g/10 a) | Herbicidal Effect* Large crabgrass | Slender amaranth | Phytotoxicity** |
|---|---|---|---|
| 400 | 4 | 5 | 0 |
| 200 | 2 | 2 | 0 |
| 0 (Blank) | 0 | 0 | 0 |

Note:
*Dead weeds percentage:
0: less than 10%
1: 10 to 30%
2: 30 to 50%
3: 50 to 70%
4: 70 to 90%
5: more than 90%
**Phytotoxicity to cotton:
0: less than 10%
1: 10 to 30%
2: 30 to 50%
3: 50 to 70%
4: 70 to 90%
5: more than 90%

EXAMPLE 2

Polyethylene vats of 1/1480 ares were charged with the field soil on which cotton seeds were sowed and then, 2 cm thick soil containing seeds of large crabgrass was placed thereon. In 3 to 4.5-leaf-stage of large crabgrass and 4.5-leaf-stage of cotton, a wettable powder prepared in Formulating Example 1 was diluted to a given concentration and was then sprinkled over the stem and the leaf in an amount of 100 liter/10a. On 16th day after seeding, the herbicidal effect and phytotoxicity to cotton were observed. The results are given in Table II. Evaluation of the herbicidal effect and the phytotoxicity was conducted as in Example 1.

TABLE II

| Concentration of compound (A) in sprinkled compositions (%) | Herbicidal Effect | Phytotoxicity |
| --- | --- | --- |
| 0.5 | 5 | 2 |
| 0.25 | 5 | 0 |
| 0 (Blank) | 0 | 0 |

EXAMPLE 3

To a test area of 3 to 4-leaf-stage Korean turf, a wettable powder prepared in Formulating Example 1 was uniformly sprinkled in an amount of 12.5 g/a. After two weeks, growth of weeds and the appearance of phytotoxicity were observed. In the area where the wettable powder was sprinkled, no weeds grew and no phytotoxicity was observed. On the contrary, in the control test area, the growth of broadleaf weeds such as lawn pennymort, common purslane and prostrate superge, and gramineous weeds such as annula bluegrass and large crabgrass was observed.

EXAMPLE 4

Polyethylene vats of 1/8850 ares were charged with the field soil on which soybean, sunflower and cotton were sowed and then, 2 cm thick soil containing weed seeds was placed. Then, a wettable powder prepared in Formulating Example 2 was uniformly sprinkled on the soil surface in a given amount. On 20th day after seeding, an herbicidal effect and phytotoxicity to soybean, sunflower and cotton were observed. The results are given in Table III.

TABLE III

| Test No. | Amount of chemicals in sprinkled compositions | | Herbicidal Effect | | | | Phytotoxicity | | |
| --- | --- | --- | --- | --- | --- | --- | --- | --- | --- |
| | Compound A (g/10 a) | Compound B (g/10 a) | Large crabgrass | Barnyard grass | Bainy galinsoga | Slender amaranth | Soybean | Sunflower | Cotton |
| 1-1 | 100 | — | 1 | 1 | 1 | 0 | 1 | 0 | 0 |
| -2 | 200 | — | 2 | 2 | 3 | 2 | 2 | 0 | 0 |
| -3 | 400 | — | 4 | 5 | 4 | 5 | 4 | 2 | 0 |
| -4 | 800 | — | 5 | 5 | 5 | 5 | 4 | 4 | 0 |
| 2-1 | — | 12.5 | 2 | 3 | 0 | 0 | 0 | 0 | 0 |
| -2 | 100 | " | 3 | 4 | 2 | 3 | 0 | 0 | 0 |
| -3 | 200 | " | 4 | 4 | 5 | 4 | 0 | 0 | 0 |
| -4 | 400 | " | 5 | 5 | 5 | 5 | 0 | 0 | 0 |
| 3-1 | — | 25 | 4 | 4 | 0 | 2 | 0 | 0 | 0 |
| -2 | 100 | " | 5 | 5 | 3 | 4 | 0 | 0 | 0 |
| -3 | 200 | " | 5 | 5 | 5 | 5 | 0 | 0 | 0 |
| -4 | 400 | " | 5 | 5 | 5 | 5 | 0 | 0 | 0 |
| 4-1 | — | 50 | 5 | 5 | 0 | 4 | 0 | 0 | 0 |
| -2 | 100 | " | 5 | 5 | 3 | 5 | 0 | 0 | 0 |
| -3 | 200 | " | 5 | 5 | 5 | 5 | 0 | 0 | 0 |
| -4 | 400 | " | 5 | 5 | 5 | 5 | 0 | 0 | 0 |
| 5 | — | — | 0 (4-leaf-stage) | 0 (4-leaf-stage) | 0 (4-leaf-stage) | 0 (2.5-leaf-stage) | 0 (1.5-leaf-stage) | 0 (4-leaf-stage) | 0 (1.5-leaf-stage) |

EXAMPLE 5

Polyethylene vats of 1/1480 ares were charged with the field soil on which cotton seeds were sowed and then, 2 cm thick soil containing weed seeds was placed. Then, wettable powders prepared in Formulating Examples 1 and 3 were diluted to a given concentration and were then sprinkled over the stem and the leaf in an amount of 100 liter/10a. When sprinkled, cotton plants were in 2-leaf-stage and weeds were 10 cm high. On 20th day after seeding, an herbicidal effect and phytotoxicity to cotton were observed. In all cases, more than 90% of bairleaf cocklebur, large crabgrass, bairy beggarticks and blue morning glory died while no phytotoxicity to cotton was observed. The results are given in Table IV.

TABLE IV

| Test No. | Concentration of Compounds in sprinkled composition (ppm) | | | Phytotoxicity to cotton | Herbicidal Effect | | | |
| --- | --- | --- | --- | --- | --- | --- | --- | --- |
| | A | C | D | | bairleaf cocklebur | large crabgrass | bairy beggarticks | blue morning glory |
| 1 | — | — | — | 0 | 0 | 0 | 0 | 0 |
| 2 | 500 | — | — | 0 | 3 | 5 | 3 | 3 |
| 3 | 1,000 | — | — | 0 | 4 | 5 | 4.5 | 4 |
| 4 | — | 250 | — | 0 | 4 | 5 | 3 | 4.5 |
| 5 | 500 | 250 | — | 0 | 5 | 5 | 5 | 5 |
| 6 | 1,000 | 250 | — | 0 | 5 | 5 | 5 | 5 |
| 7 | — | — | 500 | 0 | 4 | 2.5 | 3 | 4.5 |
| 8 | 500 | — | 500 | 0 | 5 | 5 | 5 | 5 |
| 9 | 1,000 | — | 500 | 0 | 5 | 5 | 5 | 5 |

What we claim is:

1. A method of killing weeds which consists of applying to the weeds a herbicidally effective amount of 3-[3-(4H-1,2,4-triazolyl)amino]-1-(3H)-isobenzofuranone.

2. The method according to claim 1 wherein said 3-[3-(4H-1,2,4-triazolyl)amino]-1-(3H)-isobenzofuranone is sprinkled on the soil surface in the amount of 1–5 kg per ha.

3. The method according to claim 1, wherein said 3-[3-(4H-1,2,4-triazolyl)amino]-1-(3H)-isobenzofuranone is applied to the stem or the leaf of the plants in the form of a solution containing 0.1 to 0.5% by weight of said compound.

* * * * *